United States Patent [19]
Ukon

[11] Patent Number: 5,229,611
[45] Date of Patent: Jul. 20, 1993

[54] INFRARED MICROSCOPIC SPECTROMETER USING THE ATTENUATED TOTAL REFLECTION METHOD

[75] Inventor: Juichiro Ukon, Miyanohigashi, Japan

[73] Assignee: Horiba, Ltd., Kyoto, Japan

[21] Appl. No.: 823,600

[22] Filed: Jan. 17, 1992

Related U.S. Application Data

[63] Continuation of Ser. No. 604,054, Oct. 25, 1990, abandoned.

[30] Foreign Application Priority Data

Nov. 3, 1989 [JP] Japan ................. 1-286892

[51] Int. Cl.⁵ .................. G01J 3/42; G01N 21/01
[52] U.S. Cl. .................. 250/347; 250/339; 250/353; 356/346
[58] Field of Search .......... 250/347, 360.1, 353, 250/339; 356/346, 244; 350/1.1, 1.2, 507, 511

[56] References Cited

U.S. PATENT DOCUMENTS

| | | | |
|---|---|---|---|
| Re. 32,912 | 4/1989 | Doyle | 356/244 |
| 4,547,068 | 10/1985 | Covey et al. | 356/244 |
| 4,594,509 | 6/1986 | Simon et al. | 250/353 X |
| 4,657,390 | 4/1987 | Doyle | 356/346 |
| 4,843,242 | 6/1989 | Doyle | 250/330 |
| 4,852,955 | 8/1989 | Doyle et al. | 350/1.2 |

Primary Examiner—Constantine Hannaher
Assistant Examiner—Edward J. Glick
Attorney, Agent, or Firm—Price, Gess & Ubell

[57] ABSTRACT

An infrared microscope spectrometer is used to carry out attenuated total reflection (ATR) analysis of a sample. Either the collecting element assembly or focusing element assembly is mounted for selected movement with respect to the other so as to permit alignment of the output beam from the focusing assembly with the optical axis of the spectrometer, whenever an ATR crystal with sample is placed between the collecting and focusing assemblies.

7 Claims, 2 Drawing Sheets

INFRARED MICROSCOPIC SPECTROMETER USING THE ATTENUATED TOTAL REFLECTION METHOD

This is a continuation of application Ser. No. 604,054, filed on Oct. 25, 1990, abandoned for a Infrared Microscopic Spectrometer Using the Attenuated Total Reflection Method.

BACKGROUND OF THE INVENTION

1. Field of the Invention

The present invention relates to an improved infrared microscopic spectrometer.

2. Description of Related Art

FIG. 1 shows a conventional general infrared microscopic spectrometer. Infrared rays from a light source 1 are directed to a sample 3 through a condenser mirror 2. The light transmitted through the sample 3 is focused into an image by an object mirror 4. The image is transmitted to a spectrometer system 5 to obtain a spectrum and then to a display device 6 to conduct an analysis.

Another well-known method of infrared spectrometry, the ATR (Attenuated Total Reflection) method, is used for a substance having an extraordinarily strong absorption, and thus difficult to obtain a transmission spectrum or, in the case where it is difficult to prepare a sample, to obtain the transmission spectrum.

FIG. 2 shows the basic parts of a general infrared spectrometer using the ATR method. Reference numerals 7, 8 designate a collecting mirror. Reference numerals 9, 10 designate a mirror. An optical reflecting medium having a high refractive index; for example, an ATR crystal 11 made of a refractive material, such as KRS-5, germanium and silicon, is located in an optical path between mirrors 9, 10. A sample 12 is placed on one surface of ATR crystal 11.

When infrared rays 13 from a light source (not shown) are directed upon the ATR crystal 11 by way of collecting mirror 7 and mirror 9, the rays are reflected by the contact surface between crystal 11 and sample 12. Infrared rays having certain wavelengths are absorbed by the ingredient in sample 12 that is to be measured. The infrared rays, which have passed through the ATR crystal 11, after being reflected, are directed to a spectrometer (not shown) by way of mirror 10 and collecting mirror 8 to obtain the spectrum corresponding to the ingredient to be measured.

Let us review the optical system in the above two infrared spectrometers. In the infrared microscopic spectrometer of FIG. 1, infrared rays from a light source 1 are directed to be incident upon a sample 3 by means of a condenser mirror 2. The transmitted light is then focused into an image. The condenser mirror 2 and an object mirror 4 must be coaxially arranged.

On the other hand, in the ATR method of FIG. 2, the optical axis of infrared rays incident upon the ATR crystal 11 does not coincide with the optical axis of infrared rays being reflected. As a result, the ATR method has not been applied to infrared microscopic spectrometry.

According to the prior art, for samples having strong absorption only the ATR method can be used. Microscopic spectrometry could not be used. This has led to remarkably reduced efficiency. The present invention overcomes this difficulty.

SUMMARY OF THE INVENTION

It is an object of the present invention to provide an infrared microscopic spectrometer capable of carrying out an ATR analysis in an efficient and uncomplicated manner.

In order to achieve this object and the general purpose of this invention, an infrared microscopic spectrometer utilizes a transferring mechanism capable of shifting either the collecting element assembly or the focusing-into-an image element assembly along an axis parallel to the optical axis of the spectrometer system. When an ATR crystal is disposed between the collecting element assembly and the focusing-into-an image element assembly, the transferring mechanism moves one with respect to the other until the beam output of the focusing assembly is aligned with the optical axis of the spectrometer system.

As a result, ATR analysis can be carried out by means of an infrared microscopic spectrometer, which is a very efficient apparatus. Moreover, highly accurate regulation is also possible.

BRIEF DESCRIPTION OF THE DRAWINGS

The exact nature of this invention, as well as other objects and advantages thereof, will be readily apparent from consideration of the following specification as related to the accompanying drawings, in which like reference numerals designate like parts throughout the figures thereof, and wherein.

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a microscopic spectrometer that uses the ATR method.

Figure 1:
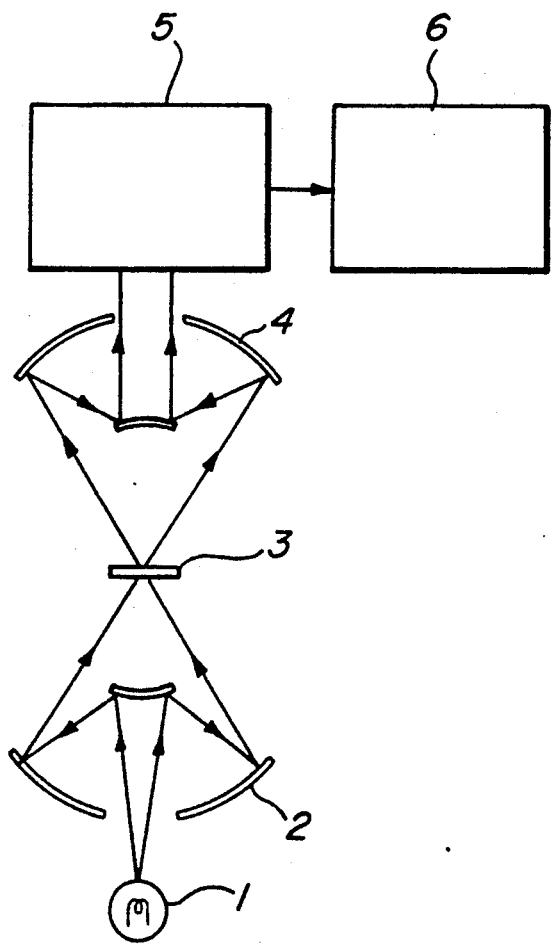
FIG. 1 is a block diagram showing a conventional transmission type infrared spectrometer.
Figure 2:
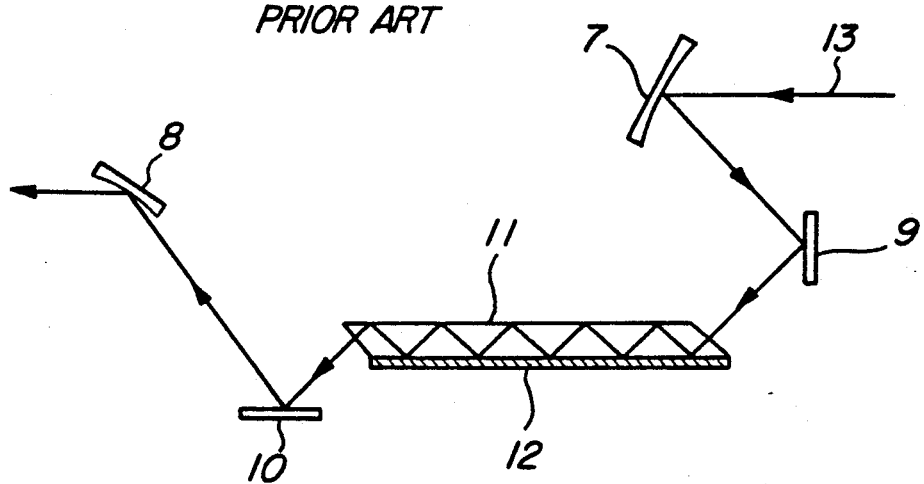
FIG. 2 is a block diagram showing a conventional infrared spectrometer using the ATR method.
Figure 3:
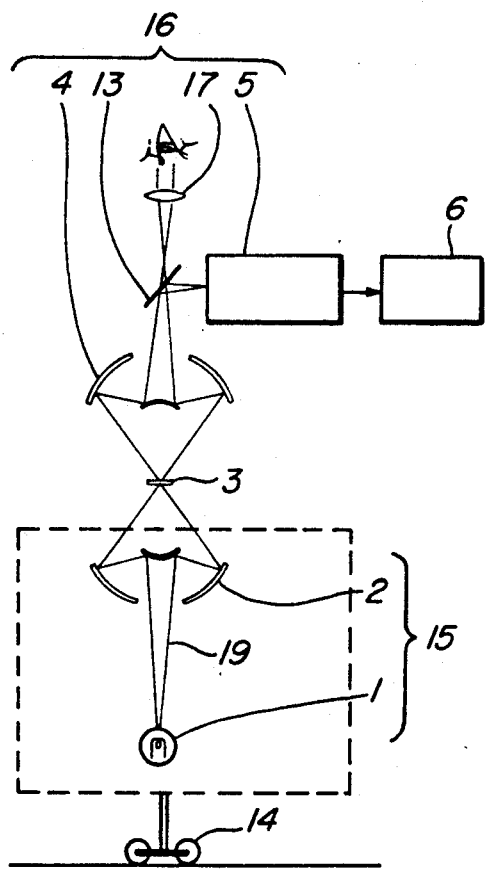
FIG. 3 is a block diagram showing a transmission type infrared microscopic spectrometer according to the present invention.
Figure 4:
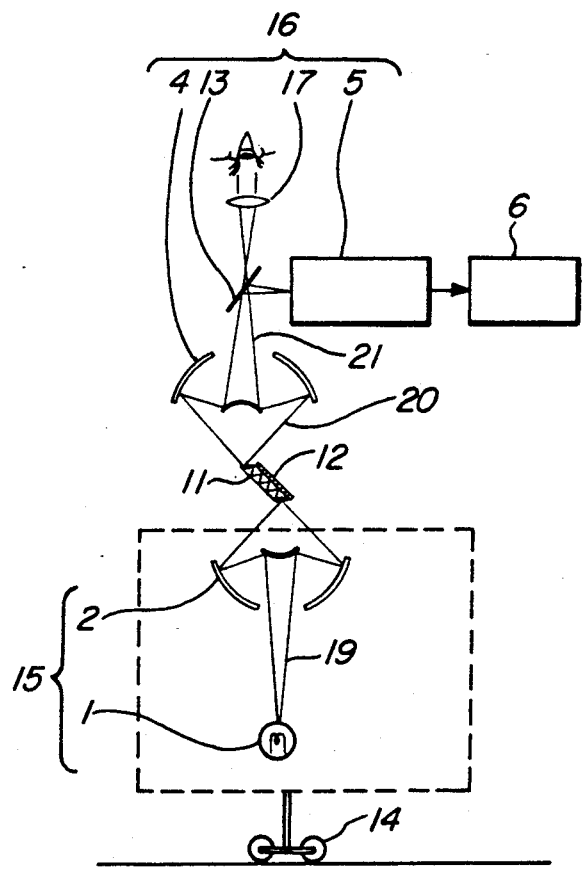
FIG. 4 is a block diagram showing an infrared microscopic spectrometer using the ATR method.

The preferred embodiment of the present invention is shown in FIGS. 3 and 4.

Referring to FIG. 3, a collecting element assembly 15 consists of a light source 1 and a condenser mirror 2. A focusing-into-an image element assembly 16 consists of an object mirror 4, a spectrometer measurement system 5, an eyepiece 17, and an optical path-change mirror 13.

Visible rays from said light source 1 are directed to be incident upon a transmission-type sample 3 through condenser mirror 2. The light transmitted through the sample 3 is focused into an image by the object mirror 4. The image of sample 3 can be observed by eyepiece 17.

When spectrometric measurement is to be carried out, the light source 1 is changed to the infrared ray side, and the optical path-change mirror 13 is located between the object mirror 4 and the eyepiece 17 to direct the light waves from the object mirror 4 to the spectrometer system 5 for analysis and then display by means of a display device 6.

The infrared microscopic spectrometer of FIG. 3 is remarkably different from the conventional infrared microscopic spectrometer in that a mechanism 14 capable of shifting the collecting elements 15 is provided. The optical axis of the collecting elements is aligned at right angles with the optical axis of the spectrometer system 5. The slide mechanism 14 manually or automatically shifts the collecting element portion 15, along a linear axis that is parallel to the optical axis of the spectrometer system 5.

When a sample must be measured by the ATR method, the present invention accommodates such a measurement, as shown in FIG. 4. The shift between the incident infrared ray 19 and the transmitted infrared ray 21 in the optical axis brought about by the ATR crystal 11 is compensated by moving the collecting element assembly 15 by means of the slide mechanism 14 so that the system can carry out a measurement in the same manner as described with respect to the transmission type infrared microscopic spectrometer of FIG. 3.

The ATR method of FIG. 4 would operate as follows. Visible rays 19 from a light source 1 collected by means of a condenser mirror 2 are directed to be incident upon an end face of ATR crystal 11, which is placed so that it is in contact with the sample 12. The light 20 emitted from crystal 11 after being reflected within the ATR crystal 11 is focused into an image by the object mirror 4. The end face of the ATR crystal 11 is observed through the eyepiece 17, thereby allowing for observation of the alignment of the light passing through the ATR crystal 11 to the optical axis. The slide mechanism 14 may be moved as required to obtain the desired alignment.

To perform the ATR analysis, the light source 1 is changed over to limit infrared rays. The infrared light rays 21 are directed to the spectrometer system 5 by means of the optical path-changing mirror 13. The spectrometer system 5 carries out the analysis.

The slide mechanism 14 may be marked at a first position for the collecting element assembly 15 for the usual samples 3 analyzed by infrared microscopy. A second position of the collecting element assembly 15 is marked for use of the system with the ATR method. As another alternative, a limit switch may be provided in the case where the slide mechanism 14 is moved by a motor or the like.

Although the collecting element assembly 15 is shown with the slide mechanism 14, the preferred embodiment contemplates that the focusing-into-an image assembly 16 could be provided with the slide mechanism 14 for focusing movement, in place of moving collecting element assembly 15. In addition, although a transmission type infrared microscopic spectrometer is described, the present invention can also be applied to a reflection type infrared microscopic spectrometer.

What has been described is a method and apparatus for performing ATR method infrared spectrometry by means of an infrared microscopic spectrometer. The invention contemplates moving either the collecting element assembly or the focusing-into-an image element assembly to bring the transmitted rays from the sample into focus with the optical axis of a spectrometer system. As a result, the optical regulation possible during measurement while using the ATR method becomes very accurate, resulting in a very efficient infrared ATR method spectrometer system.

What is claimed is:

1. In combination with an infrared microscopic spectrometer having a light source; a collecting element assembly, including a condenser mirror, said assembly being symmetric about an optical axis, for collecting infrared rays emitted from said light source and irradiating a transmission-type sample with the collected infrared rays; an object mirror assembly, symmetric about an optical axis coaxial with the optical axis of said collecting assembly, for focusing light from said sample into an image; a spectrometer measuring system for analyzing the light from said sample, the improvement comprising:

a transferring mechanism for shifting the optical axis of said collecting element assembly with respect to the optical axis of said object mirror assembly in a direction perpendicular to both said optical axes; whereby an ATR crystal may be disposed between said collecting element assembly and said object mirror assembly.

2. The infrared microscopic spectrometer of claim 1 wherein said light source alternatively provides visible light and may be switched between visible and infrared light.

3. The infrared microscopic spectrometer of claim 2 further comprising an optical path-change mirror positioned for directing light rays from the optical axis of said object mirror assembly into the optical axis of said spectrometer measurement system.

4. The infrared microscopic spectrometer of claim 3 further comprising optical lens means for visually observing light rays from said object mirror assembly while said light source is emitting visible light.

5. The infrared microscopic spectrometer comprising:

light source means for producing infrared or visible light;

light source switching means for switching said light source means between visible and infrared light;

an axially symmetric collecting mirror assembly, having an optical axis, for receiving light from said light source means and for directing said light along said axis onto a sample;

an axially symmetric object mirror assembly, having an optical axis parallel with the axis of said collecting mirror assembly, for receiving light from said sample and for directing said light along its optical axis;

a spectrometer measuring system for receiving infrared light from said object mirror assembly;

an optical lens for receiving and focusing visible light from said object mirror assembly;

beam switching means, positioned along said optical axis of said object mirror assembly, for alternatively directing said light to said optical lens or to said spectrometer measuring system, said switching means directing infrared light to said spectrometer measuring system while said light source emits infrared light and directing visible light to said optical lens while said light source emits visible light; and transferring means for moving said collecting mirror assembly relative to said object mirror assembly along an axis perpendicular to both the optical axis of the collecting mirror assembly and the optical axis of the object mirror assembly between a first position wherein said axis of said collecting mirror assembly is coaxial with said axis of said object mirror assembly whereby a transmission-type sample may be used as the sample, and a second position wherein said axis of said collecting mirror assembly is parallel to, but offset from, said axis of said object mirror assembly whereby an ATR crystal may be used as the sample.

6. A microscopic spectrometer comprising:
light source means for generating a beam of light;
an axially symmetric collecting mirror assembly, having an optical axis, for receiving light from said light source means and for directing said light along its axis onto a sample;
an axially symmetric object mirror assembly, having an optical axis parallel with the axis of said collecting mirror assembly, for receiving light from said sample and for directing said light along its optical axis;
a spectrometer measuring means for receiving infrared light from said object mirror assembly; and
transferring means for moving said collecting mirror assembly relative to said object mirror assembly along an axis perpendicular to both the optical axis of the collecting mirror assembly and the optical axis of the object mirror assembly between a first position wherein said axis of said collecting mirror assembly is coaxial with said axis of said object mirror assembly whereby a transmission-type sample may be used as the sample, and a second position wherein said axis of said collecting mirror assembly is offset from said axis of said object mirror assembly whereby an ATR crystal may be used as said sample.

7. The optical system of claim 6 wherein said light source is capable of emitting visible or infrared light and wherein said optical system further comprises:
light source switching means for switching said light source means between visible and infrared light; and
beam switching means, positioned along said optical axis of said object mirror assembly, for alternatively directing said light to an optical lens for focussing said visible light or to said spectrometer measuring means, said switching means directing infrared light to said spectrometer measuring system while said light source emits infrared light and directing visible light to said optical lens while said light source emits visible light.

* * * * *